United States Patent

Ponsold et al.

[11] 4,029,648
[45] June 14, 1977

[54] PROCESS OF MAKING GONA-1,3,5(10),9(11)-TETRAENES

[75] Inventors: Kurt Ponsold; Helmut Kasch, both of Jena, Germany

[73] Assignee: VEB Jenapharm, Jena, Germany

[22] Filed: Jan. 15, 1976

[21] Appl. No.: 649,465

[52] U.S. Cl. .............. 260/239.55 R; 260/397.45; 260/397.5; 260/239.55 C
[51] Int. Cl.² ........................................ C07J 17/00
[58] Field of Search ................ 260/397.45, 397.5

[56] References Cited
UNITED STATES PATENTS

| | | | |
|---|---|---|---|
| 3,385,872 | 5/1968 | Alyarez | 260/397.45 |
| 3,720,694 | 3/1973 | Junghans et al. | 260/397.5 |

*Primary Examiner*—Elbert L. Roberts
*Attorney, Agent, or Firm*—Michael J. Striker

[57] ABSTRACT

Gona-1,3,5(10),9(11)-tetraenes having the formula

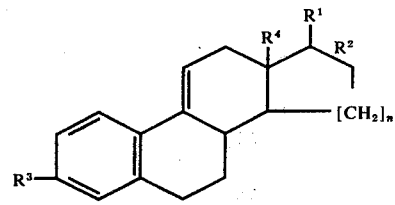

in which formula
n is 1 or 2,
$R^1$ is a hydrogen, hydroxy, alkoxy, or alkanoyl substituent,
$R^2$ is a hydrogen, alkoxy, acetoxy, alkyl, akenyl, or alkynyl substituent, or a substituent having the formula —$CH_2X$ in which X is a halogen, pseudohalogen, or O-alkyl substituent, or
$R^1$ or $R^2$ together are oxygen, or a methyleneoxy or ethylenedioxy substituent,
$R^3$ is a hydroxy, alkoxy, alkanoyl, or alkoxymethyleneoxy substituent, and
$R^4$ is a methyl or ethyl substituent,
are made from gona-1,3,5(10)trienes by electrolysis of a solution thereof in water and/or a primary or secondary alcohol in the presence of an electroconductive compound.

The gona-1,3,5(10),9(11)-tetraenes are intermediates for the production of steroidal pharmaceuticals for fertility control in human and animal therapeutics.

9 Claims, No Drawings

PROCESS OF MAKING GONA-1,3,5(10),9(11)-TETRAENES

BACKGROUND OF THE INVENTION

The present invention pertains to a process of making gona-1,3,5-(10),9(11)-tetraenes such as those having the following formula

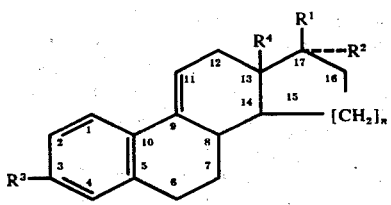

in which formula
$n$ is 1 or 2,
$R^1$ is a hydrogen, hydroxy, alkoxy, pyranyloxy, or alkanoyl substituent,
$R^2$ is a hydrogen, alkoxy, acetoxy, alkyl, alkenyl, or alkynyl substituent, or a substituent having the formula —$CH_2X$ in which X is a halogen, pseudohalogen, or O-alkyl substituent, or
$R^1$ and $R^2$ together are oxygen, or a methyleneoxy or ethylenedioxy substituent,
$R^3$ is a hydroxy, alkoxy, alkanoyl, or alkoxymethyleneoxy substituent, and
$R^4$ is a methyl or ethyl substituent.

The preparation of 3-hydroxy-13β-methylgona-1,3,5(10),9(11)-tetraen-17-one and 3-methoxy-13β-methylgona-1,3,5(10),9(11)-tetraen-17-one by reactions of 3-hydroxy-13β-methylgona-1,3,5(10)-triene and 3 methoxy-13β-methylgona-1,3,5(10)-triene, respectively, with 2,3-dichloro-5,6-dicyanobenzoquinone has been described by W. Brown, J. W. A. Findlay, and A. B. Turner in Chemical Communications, 1968, pages 10–11, and with adamantanol by W. H. Lunn and E. Farkas in Tetrahedron, vol. 24, pages 6773–6776 (1968).

The preparation of 3-hydroxy-13β-methylgona-1,3,5(10),9(11)-tetraen-17-one and 3-alkyl ethers thereof by reaction of 3-hydroxy-13β-methylgona-1,3,5(10)-trien-17-one with antimony pentafluoride and fluosulfonic acid was described by J. P. Gesson, J. C. Jacquesy and R. Jacquesy in Tetrahedron Letters No. 49, pages 4733–4736 (1971).

Although yields between 60 and 70% of the theoretical can be obtained in accordance with the foregoing processes, they have the disadvantage that expensive reagents or reagents that are not suitable for commercial use are required. Another disadvantage of these processes for the production of gona-1,3,5(10),9(11)-tetraenes from 3-hydroxy-13β-methylgona-1,3,5(10)-trienes are the reactions with chlorine, bromine, or iodine that are required to produce these compounds, either in a 2-step process from 10β-chloro-13β-methylgona-1,4-dien-3-one or in a synthesis involving the production of 3,3-(1-oxo-2-methylpropylene-1,2-dioxy)-10β-bromo-13β-methylgona-1,4-diene or the corresponding iodo compound. Higher yields can be obtained only by large expenditures for syntheses, whereas lower yields are obtained with the less-used processes.

It is also known that 3-methoxy-13β-methylgona-1,3,5(10),8(9)-tetraene that can be obtained by total synthesis can be partially converted to 3-methoxy-13β-methylgona-1,3,5(10),9(11)-tetraene. Since this rearrangement is not complete, and both isomers are difficult to separate from each other, this process is of little importance.

A further possibility of introducing a 9(11) double bond in gona-1,3,5(10)-trienes consist in dehydrating an 11-hydroxy-13β-methylgona-1,3,5(10)-triene. Since 11-hydroxy-13β-methylgona-1,3,5(10)-trienes however are not readily accessible, this process also is of little importance for the preparation of 13β-methylgona-1,3,5(10),9(11)-tetraenes from readily producible 13β-methylgona-1,3,5(10)-trienes.

SUMMARY OF THE INVENTION

The object of the present invention is to provide economically feasible processes for the production of gona-1,3,5(10),9(11)-tetraenes.

In accordance with the processes of the present invention, substituted gona-1,3,5(10),9(11)-tetraenes are produced from substituted gona-1,3,5(10)-trienes. These processes are relatively simple with respect to the apparatus required, as well as operational steps, and the original substituents of the gona-1,3,5(10)-trienes remain unchanged throughout the process.

The processes of the present invention comprise the step of electrolyzing a solution of a gona-1,3,5(10)-triene having the formula

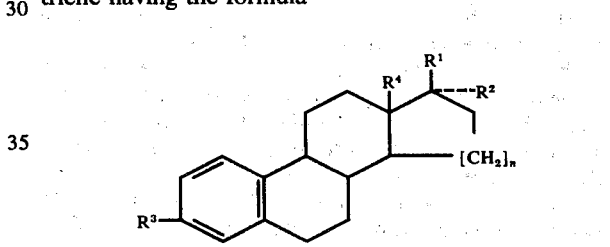

in which formula
$n$ is 1 or 2,
$R^1$ is a hydrogen, hydroxy, alkoxy, pyranyloxy, or alkanoyl substituent,
$R^2$ is a hydrogen, alkoxy, acetoxy, alkyl, alkenyl, or alkynyl substituent, or a subsituent having the formula —$CH_2X$ in which X is a halogen, pseudohalogen, or O-alkyl substituent, or
$R^1$ and $R^2$ together are oxygen, or a methyleneoxy or ethylenedioxy substituent,
$R^3$ is a hydroxy, alkoxy, alkanoyl or alkoxymethyleneoxy substituent, and
$R^4$ is a methyl or ethyl substituent.

The solvent in which the gona-1,3,5(10)-triene is dissolved is water, a primary or secondary alcohol, or a mixture thereof. The solution also includes one or more electroconductive compounds that are inert with respect to the gona-1,3,5(10)-triene and are stable under the conditions of the electrolysis, as well as a protonacceptor and, if necessary, a solubilizer.

The electrolysis is conducted with an electric current of constant strength or of constant intensity.

As a result of the electrolysis, the gona-1,3,5(10)-triene is converted to two new compounds which are 9α and 9β-alkoxy or hydroxy gona-1,3,5(10)-trienes having the following two respective formulae

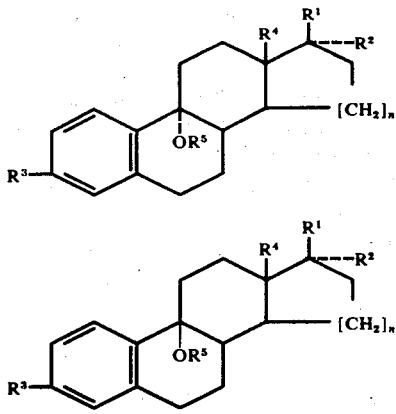

in which formulae

R⁵ is a hydrogen, methyl, ethyl, n-propyl or isopropyl substituent, and $n$, $R^1$, $R^2$, $R^3$ and $R^4$ have the same significance as hereinbefore.

These intermediate compounds can each be easily isolated as such and be converted by treatment with an acid catalyst into a gona-1,3,5(10),9(11)-tetraene that does not contain the 9α or 9β substituent, or the electrolyzed solution can itself be subsequently treated directly with an acid catalyst to produce the gona-1,3,5(10),9(11)-tetraene that does not contain the 9α or 9β substituent. This conversion proceeds into the presence of acid catalysts such as acid alumina, silica gel, organic acids or dilute mineral acids.

The electroconductive compounds that are required in the processes of the present invention must be stable under those conditions prevailing during the electrolysis and must not react with the gona-1,3,5(10)-trienes. Cationic moieties of these electroconductive compounds may be ions of the alkali and alkaline-earth metals as well as cations of other metals and oxonium salts of elements of Groups V and VI of the Periodic Table, and the anionic moieties of the electroconductive compounds may be fluoborate, sulfate, perchlorate, arylsulfonate, alkylsulfonate, alkoxide, hexafluorophosphate, hydroxyl, nitrate, or carboxyl ions.

Solvents which also are nucleophilic reagents that may be used are water and primary and secondary alcohols, for example, methanol, ethanol, n-propanol and isopropanol.

Proton-acceptors which under the prevailing electolysis conditions can be used in the processes of the present invention are such organic bases as pyridine, picolines, lutidine (2,6-dimethylpyridine and other dimethylpyridines), collidine (2,4,6-trimethylpyridine and other trimethylpyridines) and hydroxyl and carboxyl ions, as well as salts of weak mineral acids.

The addition of other solvents that serve as solubilizers for the gona-1,3,5(10)-triene and gona-1,3,5(10),9(11)-tetraene in alcohol or water and at the same time increase the electrical conductivity of the solution in the electrolytic cell is advantageous. For this purpose, ethers such as diethyl ether, tetrahydrofuran, dioxane, ethyl acetate, acetonitrile, and N,N-dimethylformamide, dimethyl sulfoxide, acetone, methyl ethyl ketone, chlorinated hydrocarbons such as dichloromethane, chloroform and trichloroethylene, tertiary alcohols, nitromethane and nitrobenzene can be used.

The electrolysis can be conducted in a cell without partitions or diaphragms separating the anode from the cathode. Dependent upon the stability of the compound that is to be oxidized, the solvent, and the electroconductive compound, the electrolysis is conducted at a constant current or constant voltage. When the electrolysis is conducted with a constant current, alternating, rectified unsmoothed alternating, direct, or modulated direct currents can be used. Direct current must be used if the electrolysis is to be conducted with a constant voltage.

The conditions of the electrolysis, such as current amperage, current density, surface area of the electrodes, as well as pressure and temperature, can be varied within wide ranges. The electrolysis will preferably be effected at a current density between $1 \times 10^{-4}$ and 0.1 ampere per square centimeter.

The electrodes must conduct the electric current and be stable under the conditions of the electrolysis. Preferably electrodes of a noble metal such as platinum or lead dioxide are used.

The concentration of the electroconducting compound and the gona-1,3,5(10)-triene that is to be oxidized can also be varied within a wide range. The electolysis will not be disturbed if a portion of the gona-1,3,5(10)-triene that is to be oxidized is present as a solid phase, such as, for example, in a saturated solution.

It was surprising that such sterically complicated molecules as the gona-1,3,5(10)-trienes which could include constituents of various kinds could under the reaction conditions disclosed herein be converted by such selective electrochemical oxidation into 9-hydroxy or 9-alkoxy gona-1,3,5(10)-trienes. These reactions, namely, first to form the intermediate 9-hydroxy or 9alkoxy gona-1,3,5(10)-trienes and then selectively converting them to the desired gona-1,3,5(10),9(11)-tetraene, are effected under milder conditions than are normally required in chemical reactions with other reagents.

The processes of the present invention have the advantage that they can be performed with relatively inexpensive apparatus and without expensive reagents and that the required electrolysis can be completed within a relatively short period to produce very good yields of the desired products.

The compounds produced in accordance with the processes disclosed herein are of pharmcological interest because of their structural relationships to biologically active steroidal hormone derivatives and are at the same time important intermediates for the preparations of new steroidal pharmaceuticals for fertility control in human and animal therapeutics. See e.g. U.S. Pat. No. 3,408,372; British Pat. No. 1,129,991 and West German Published Applications 1,618,815, 1,618,829 and 1,618,830.

DETAILED DESCRIPTION AND PREFERRED EMBODIMENTS OF THE INVENTION

The invention is further described in connection with the examples which follow which were selected solely for purposes of illustration and consequently are not to be construed as restrictive of the invention.

EXAMPLE 1

3-Methoxy-13β-methylgona-1,3,5(10),9(11)-tetraen-17-one.

A solution of 2.3 grams of 3-methoxy-13β-methylgona-1,3,5(10)-triene 17-one, 1.1 milliliters of 2,6- dimethylpyridine and 0.7 gram of sodium perchlorate in 45 milliliters of methanol and 15 milliliters of dichloromethane was electrolyzed between platinum electrodes, the anode having a surface area of 21 square centimeters and the cathode having a surface area of 4 square centimeters, which were spaced apart from each other at a distance of about 1.5 centimeters, with a current of 800 milliamperes for 40 minutes.

The solution was then made slightly acid by the addition of hydrochloric acid thereto and allowed to stand at room temperature for a period between 20 and 30 minutes. The dichloromethane was then distilled therefrom and, from the remaining solution, 2.0 grams of 3-methoxy-13β-methylgona-1,3,5(10),9(11)-tetraen-17-one having a melting point of 140°–142° C, was crystallized. After recrystallization from a mixture of methanol and dichloromethane, 1.9 grams of the analytically pure compound, which has a melting point of 144.5°–146° C and a specific optical rotation of +305.5° at a temperature of 25° C for the sodium D line, was obtained.

EXAMPLE 2

3-Methoxy-13β-methylgona-1,3,5(10),9(11)-tetraen-17-one and 3,9α and 3,9β-dimethoxy-13β-methylgona-1,3,5(10)-trien-17-ones.

A solution containing 2.3 grams of 3-methoxy-13β-methylgona-1,3,5(10)-trien-17-one containing the other constituents that were described in Example 1 was electrolyzed for 40 minutes in the same manner as described in Example 1. Water was then added to the resulting solution and the mixture was extracted with dichloromethene. The dichloromethane extracts were then evaporated to dryness and the residue taken up and recrystallized from methanol. In this manner, 1.3 grams of 3,9α-dimethoxy-13β-methylgona-1,3,5(10)-trien-17-one, having a melting point of 107°–109° C. and a specific optical rotation of +117.7° at a temperature of 25° C. for the sodium D line, was obtained.

The mother liquor still contained 3,9β-dimethyoxy-13β-methylgona-1,3,5(10)-trien-17-one which was recovered by distilling off the solvent and crystallizing the residue from a mixture of dichloromethane and n-hexane. In this manner, 0.6 gram of that compound, which had a decomposition point of 121° C. and a specific optical rotation of +62.3° at a temperature of 25° C. for the sodium D line, was obtained.

A solution of 0.25 gram of the 3,9α-dimethoxy-13β-methylgona-1,3,5(10)-trien-17-one that was prepared as described hereinbefore dissolved in 8 milliliters of methanol and 2 milliliters of dichloromethane was made slightly acid by adding hydrochloric acid thereto and the thus acidified solution was allowed to stand for between 20 and 30 minutes, after which the dichloromethane was distilled therefrom, leaving 0.23 gram of 3-methoxy-13β- -methylgona-1,3,5(10),9(11)-tetraen-17-one having a melting point of 141°–143° C.

The same amount of 3-methoxy-13β-methylgona-1,3,5(10),9(11)-tetraen-17-one was obtained when 3,9β-dimethoxy-13β-methylgona-1,3,5(10)-trien-17-one that was prepared as described hereinbefore was substituted in the foregoing preparation for the same amount of 3,9α-dimethoxy-13β-methylgona-1,3,5(10)-trien-17-one therein.

EXAMPLE 3

3-Methoxy-13β-methyl-1,3,5(10),9(11)-tetraen-17-one.

A solution of 3.0 grams of 3-methoxy-13β-methyl-gona-1,3,5(10)-trien-17-one and 0.66 gram of sodium acetate in 60 milliliters of methanol and 20 milliliters of dichloromethane was electroyzed between the same platinum electrodes as specified in Example 1 while a potential of 1.7 volts (measured at the anode against a standard saturated calomel electrode) was maintained between the electrodes. At the completion of the electrolysis, which was established by thin-layer chromatography, the solution was made slightly acid by adding sulfuric acid thereto and it was allowed to stand at room temperature for a period between 20 and 30 minutes. Thereafter the dichloromethane was distilled and the product was crystallized from the remaining methanolic solution. In this manner, 2.5 grams of 3-methoxy-13β-methylgona-1,3,5(10),9(11)-tetraen-17-one having a melting point of 142°–145° C. was obtained.

EXAMPLE 4

3-Methoxy-13β-methylgona-1,3,5(10),9(11)-tetraen-17-one and 3,9α and 3,9β-dimethoxy-13β-methylgona 1,3,5(10)-trien-17-ones.

A solution containing 3 grams of 3-methoxy-13β-methylgona-1,3,5(10)-trien-17-one was electrolyzed exactly as described in Example 3. At the end of the electrolysis, a saturated solution of sodium bicarbonate was added thereto and the mixture was extracted with dichloromethane. After separation of the dichloromethane phase from the aqueous phase, the dichloromethane phase was dried over anhydrous sodium sulfate and the solvent was then distilled off at a subatmospheric pressure. After recrystallizing the residue from methanol, 1.5 grams of 3,9α-dimethoxy-138-methyl-gona-1,3,5(10),9(11)-tetraen-17-one having a melting point of 104°–108° C and a specific optical rotation of +117.7° at a temperature of 25° C for the sodium D line, was obtained.

After distilling off the solvent from the mother liquor and recrystallizing the residue from a mixture of dichloromethane and n-hexane, 0.7 gram of 3,9β-dimethoxy-13β-methylgona-1,3,5(10)-trien-17-one was recovered, which had a decomposition point of 121° C and a specific optical rotation of +62.3° at a temperature of 25° C for the sodium D line.

Both the 3,9β-dimethoxy and the 3,9α-dimethoxy-13β-methylgona-1,3,5(10)-trien-17-ones were converted to 3-methoxy-13β-methylgona-1,3,5(10),9(11)-tetraen-17-one by the same procedure described in Example 2 hereinbefore.

EXAMPLE 5

3-Methoxy-13β-methylgona-1,3,5(10),9(11)-tetraen-17-one.

A solution of 0.5 gram of 3-methoxy-13β-methyl-gona-1,3,5(10)-trien-17-one, 0.5 milliliter of 2,6-dimethylpyridine, 1.97 grams of tetrabutylammonium fluoborate [$(C_4H_9)_4N$-$BF_4$] in 40 milliliters of acetonitrile, 10milliliters of water and 10 milliliters of tetrahydrofuran was electrolyzed between a platinum anode having a surface area of 21 square centimeters and a nickel cathode having a surface area of 20 square centimeters while a potential of 1.7 volts measured at the anode against a saturated calomel standard electrode was maintained between the electrodes. At the completion of the electrolysis, which was established by thin-layer chromatography, the electrolyte solution was made slightly acid by adding hydrochloric acid thereto and the acidified solution was then allowed to stand at room temperature for a period between 20 and 30 minutes. Water was then added to the solution and the mixture was then extracted with diethyl ether. The ether layer was then separated, dried over anhydrous sodium sulfate, and the solid was distilled therefrom at a subatmospheric pressure. The residue was taken up in a mixture of dichloromethane and methanol and recrystallized therefrom. In this manner, 0.3 gram of 3-methoxy-13β-methylgona-1,3,5(10),9(11)-tetraen-17-one having a melting point of 139°–143° C was obtained.

EXAMPLE 6

3-Methoxy-13β-methylgona-1,3,5(10),9(11)-tetraen-17-one and 3-methyl-9β and 3-methyl-9β-hydroxy-13β-methylgona-1,3,5(10)-trien-17-ones.

Another batch of the same solution as specified in Example 5 was electrolyzed as described in Example 5 and, after the electrolysis, water was added to the solution and the mixture was extracted with diethyl ether, the ether extract was separated, dried over anhydrous sodium sulfate, and the solvent distilled therefrom at a subatmospheric pressure, all as described in Example 5.

The residue was dissolved and the solution was subjected to chromatographic separation, using a chromatographic column having a length of 15 centimeters and a diameter of 2 centimeters filled with a chromatographic grade of silicate gel and eluents consisting of mixtures of benzene and diethyl ether in volumetric ratios between 20 : 1 and 1 : 1, respectively. 3-Methoxy-9α-hydroxy-13β-methygona-1,3,5(10)-trien-17-one was the principal product in the first eluate. By concentrating this eluate and crystallizing the oily residue from a mixture of acetone and water, 0.2 gram of that compound having a decomposition point of 145° C and a specific optical rotation of +167.7° at a temperature of 25° C for the sodium D line, was obtained.

From the second eluate, 0.1 gram of 3-methoxy-9β-hydroxy-13β-methylgona-1,3,5(10)-trien-17-one having a melting point of 69°–74° C and a specific optical rotation of +35.4° at a temperature of 25° C for the sodium D line, was obtained in the same manner as described hereinbefore.

Solutions of 1 gram of each of these 3-methoxy-9α-hydroxy and 3-methoxy-9β-hydroxy 13β-methylgona-1,3,5(10)-trien-17-ones that were thus recovered were dissolved in 8 milliliters of methanol and 2 milliliters of dichloromethane and the solutions were made slightly acid by adding hydrochloric acid thereto. After allowing each of the said solutions to stand for a period between 20 and 30 minutes at room temperature, the dichloromethane was distilled from each and the products were crystallized from the remaining solutions. In this manner, 0.9 gram of the same 3-methoxy-13β-methylgona-1,3,5(10),9(11)-tetraen-17-one having a melting point of 142°–145° C was obtained from each of these compounds.

EXAMPLE 7

3-Methoxy-13β-methylgona-1,3,5(10),9(11)-tetraen-17-one.

A solution of 0.5 gram of 3-methoxy-13β-methylgona-1,3,5(10)-trien-17-one. 1.1 milliliters of 2,6-dimethylpyridine and 0.7 gram of sodium perchlorate in 45 milliliters of ethanol and 15 milliliters of dichloromethane was electrolyzed with the same platinum electrodes and under the same conditions as described in Example 3 hereinbefore and the electrolyzed solution was made slightly acid with hydrochloric acid and allowed to stand at room temperature for 20 minutes. The dichloromethane was distilled therefrom at a subatmospheric pressure and crystals were allowed to form in the remaining solution. In this manner, 0.4 gram of 3-methoxy-13β-methylgona-1,3,5(10),9(11)-trien-17-one having a melting point of 144°–146° C was obtained.

EXAMPLE 8

3-Methoxy-13β-methylgona-1,3,5(10),9(11)-tetraen-17-one.

The procedure described in Example 7 was repeated but an equal volume of n-propanol was substituted for the ethanol used in that example. In this example 0.35 gram of 3-methoxy-13β-methylgona-1,3,5-(10),9(11)-tetraen-17-one having a melting point of 140°–143° C was obtained.

EXAMPLE 9

3-Methoxy-13β-methyl-17β-acetoxygona-1,3,5(10),9(11)-tetraene.

The procedure described in Example 1 hereinbefore was repeated but an equal amount of 3-methoxy-13β-methyl-17β-acetoxygona-1,3,5(10)-triene was substituted for the 3-methoxy-13β-methylgona-1,3,5(10)-trien-17-one that was used in that example. After distilling off the dichloromethane from the electrolyzed solution at a subatmospheric pressure and crystallizing from the remaining solution, 2.0 grams of 3-methoxy-13β-methyl-17β-acetoxygona-1,3,5(10),9(11)-tetraene having a melting point of 110°–113° C, was obtained. After recrystallization of the compound from a mixture of dichloromethane and methanol it had a melting point of 114°–116° C and a specific optical rotation of +95° at a temperature of 25° C for the sodium D line.

EXAMPLE 10

3-n-Propoxy-13β-methylgona-1,3,5(10),9(11)-tetraen-17-one.

The procedure described in Example 1 hereinbefore was repeated except that 1 gram of 3-n-propoxy-13β-methylgona-1,3,5(10)-trien-17-one was substituted for the 2.3 grams of 3-methoxy-13β-methylgona-1,3,5(10),9(11)-trien-17-one that was used in that example and the electrolysis was effected with a current of 80 milliamperes for 20 minutes.

After distilling off the dichloromethane from the electrolyzed solution at a subatmospheric pressure and the addition of a small amount of water to the remaining solution, 0.8 gram of 3-n-propoxy-13β-methylgona-1,3,5(10),9(11)-tetraen-17-one precipitated which, after recrystallization from aqueous methanol, had a melting point of 77.5°–78.5° C and a specific optical rotation of +266.2° at a temperature of 25° C for the sodium D line.

EXAMPLE 11

3-Isobutoxy-13β-methylgona-1,3,5(10),9(11)-tetraen-17-one.

The procedure described in Example 10 hereinbefore was repeated except that 1 gram of 3-isobutoxy-13β-methylgona-1,3,5(10)-trien-17-one was substituted for the 3-n-propoxy-13β-methylgona-1,3,5(10)-trien-17-one that was used in that example. In this manner, 0.8 gram of 3-isobutoxy-13β-methylgona-1,3,5(10),9(11)-tetraen-17-one was obtained after distillation of the dichloromethane from the electrolyzed solution and precipitation by adding a small amount of water to the remaining solution. This compound, after recrystallization from a mixture of dichloromethane and methanol, had a melting point of 107°–108° C and a specific optical rotation of +257.5° at a temperature of 25° C for the sodium D line.

EXAMPLE 12

3-Methoxy-13β-methylgona-1,3,5(10),9(11)-tetraen-17β-ol.

The procedure described in Example 1 hereinbefore was repeated except that 2.3 grams of 3-methoxy-13β-methylgona-1,3,5(10)-trien-17β-ol was substituted for the 3-methoxy-13β-methylgona-1,3,5(10)-tetraen-17-one in that example.

In this manner, 1.95 grams of 3-methoxy-13β-methylgona-1,3,5(10),9(11)-tetraen-17β-ol was obtained after distillation of the dichloromethane from the electrolyzed solution and precipitation by adding a small amount of water to the remaining solution. This compound, after recrystallization from a mixture of dichloromethane and methanol had a melting point of 95°–97° C and a specific optical rotation of +142.1° at a temperature of 25° C for the sodium D line.

EXAMPLE 13

3,17β-Dimethoxy-13β-methylgona-1,3,5(10),9(11)-tetraene.

The procedure described in Example 1 hereinbefore was repeated except that 2.3 grams of 3,17β-dimethoxy-13β-methylgona-1,3,5(10)-triene was substituted for the 3-methoxy-13β-methylgona-1,3,5(10)-trien-17-one in that example.

In this manner, 2.0 grams of 3,17β-dimethoxy-13β-methylgona-1,3,5(10),9(11)-tetraene having a melting point of 146°–149° C was crystallized out of the methanolic solution remaining after the dichloromethane was distilled from the solution following its electrolysis. This compound, after recrystallization from a mixture of dichloromethane and methanol, had a melting point of 149°–150.5° C and a specific optical rotation of +130.5° at a temperature of 25° C for the sodium D line.

EXAMPLE 14

3-Methoxy-13β-methyl-17,17-(ethylenedioxy)gona-1,3,5(10),9(11)-tetraene.

The procedure described in Example 1 hereinbefore was repeated except that 2.3 grams of 3-methoxy-13β-methyl-17,17-(ethylenedioxy)gona-1,3,5(10)-triene was substituted for the 3-methoxy-13β-methylgona-1,3,5(10)-trien-17-one in that example.

After the solution had been electrolyzed it was evaporated to dryness and the residue was chromatographed using acid alumina granules in a column having a length of 30 centimeters and a diameter of 2 centimeters that was eluted with benzene. The benzene eluate was concentrated by evaporation and the residue was crystallized from a mixture of diethyl ether and petroleum ether. In this manner, 1.2 grams of 3-methoxy-13β-17,17-(ethylenedioxy)gona-1,3,5(10),9(11)-tetraene, having a melting point of 149°–151° C and a specific optical rotation +96.6° at a temperature of 25° C for the sodium D line, was obtained.

EXAMPLE 15

3-Methoxy-13β-methyl-17,17-(ethylenedioxy)gona-1,3,5-(10),9(11)-tetraene.

A solution of 2.3 grams of 3-methoxy-13β-methyl-17,17-(ethylenedioxy)gona-1,3,5(10)-triene, 1.1 milliliters of 2,6-dimethylpyridine, and 1.4 grams of tetraethylammonium perchlorate in 45 milliliters of N,N-dimethylformamide and 50 milliliters of methanol was electrolyzed between the same pair of electrodes that were described in Example 1, spaced from each other at a distance of 1.5 centimeters, with a current of 600 milliamperes for a period of 55 minutes. At the end of the electrolysis all traces of methanol were distilled from the solution at a subatmospheric pressure and the solution was then acidified with anhydrous p-toluenesulfonic acid, allowed to stand at room temperature for a period between 20 and 30 minutes and then made alkaline with a saturated solution of sodium bicarbonate. A portion of the product precipitated during the addition of the bicarbonate solution and water was then added to complete its precipitation. In this manner, 1.8 grams of 3-methoxy-13β-methyl-17,17-(ethylenedioxy)gona-1,3,5-(10),9(11)-tetraene having a melting point of 146°–149° C was obtained.

EXAMPLE 16

3-Methoxymethyleneoxy-13β-methylgona-1,3,5(10),9(11)-tetraen-17-one.

The procedure described in Example 15 was repeated except that 2.3 grams of 3-methoxymethyleneoxy-13β-methylgona-1,3,5(10)-triene was substituted for the 3-methoxy-13β-methyl-17,17-(ethylenedioxy)gona-1,3,5(10)-triene used therein.

In this manner, 1.8 grams of analytically pure 3-methoxymethyleneoxy-13β-methylgona-1,3,5(10),9(11)tetraen-17-one, having a melting point of 135°–137.5° C and a specific optical rotation of +268.8° at a temperature of 25° C for the sodium D line, when the product was recrystallized from a mixture of dichloromethane and n-hexane, was obtained.

EXAMPLE 17

3-Methoxy-13β-methyl-17β-acetoxy-D-homogona-1,3,5(10),9(11)-tetraene.

A solution of 0.1 gram of 3-methoxy-13β-methyl-17β-acetoxy-D-homogona-1,3,5(10)-triene, 0.5 milliliter of 2,6-dimethylpyridine and 1.4 grams of tetraethylammonium perchlorate in 45 milliliters of N,N-dimethylformamide and 15 milliliters of methanol was electrolyzed with a platinum electrodes according to the method described in Example 3 hereinbefore.

The electrolyte solution was then made slightly acid by addition of hydrochloric acid thereto and the acid solution was allowed to stand at room temperature for a period between 20 and 30 minutes, after which water was added and the mixture was extracted with dry ethyl ether. The ether extract was then dried over anhydrous sodium sulfate and the solvents were distilled therefrom at a subatmospheric pressure. The residue was dissolved and recrystallized from a mixture of dichloromethane and methanol. In this manner, 0.06 gram of racemic 3-methoxy-13β-methyl-17β-acetoxy-D-homogona-1,3,5(10),9(11)-tetraene having a melting point of 173°–177° C was obtained. This compound had two ultraviolet maxima at 264 (log ε 4.2) and 297 (log ε 3.5) micromillimeters (millimicrons).

EXAMPLE 18

3-Methoxy-13β-methyl-17α-azidomethylgona-1,3,5(10),9(11)-trien-17β-ol.

A solution of 0.5 gram of 3 methoxy-13β-methyl-17α-azidomethylgona-1,3,5(10)-trien-17β-ol, 1.1 milliliters of 2,6-dimethylpyridine, and 0.7 gram of sodium perchlorate in 45 milliliters of methanol and 15 milliliters of dichloromethane was electrolyzed with a platinum anode and a nickel cathode wxactly as described in Example 5 hereinbefore. The conclusion of the electrolysis was evidenced both by thin-layer chromatography as well as by the strong decrease of the flow of current during the electrolysis.

The electrolyzed solution was then made slightly acid by addition of perchloric acid thereto and allowed to stand at room temperature for a period between 20 and 30 minutes. The dichloromethane was then distilled off at a subatmospheric pressure and water was added to the remaining methanolic solution to precipitate the product. In this manner, 0.3 gram of 3-methoxy-13β-methyl-17α-azidomethylgona-1,3,5(10),9(11)-tetraen-17β-ol was obtained which, after recrystallization from aqeuous methanol, had a melting point of 112°–114° C and a specific optical rotation of +105.8° at a temperature of 25° C for the sodium D line.

EXAMPLE 19

3-Methoxy-13β,17α-dimethylgona-1,3,5(10),9(11)-tetraen-17β-ol.

The procedure described in Example 18 hereinbefore was repeated except that 0.5 gram of 3 methoxy-13β,17α-dimethylgona-1,3,5(10)-trien-17β-ol was substituted for the 3-methoxy-13β-methyl-17α-azidomethylgona-1,3,5(10)-trien-17β-ol in that example.

In this example, 0.35 gram of 3-methoxy-13β,17α-dimethylgona-1,3,5(10),9(11)-trien-17β-ol, having a melting point of 75°–78° C and a specific optical rotation of +103.9° at a temperature of 25° C for the sodium D line, was obtained.

EXAMPLE 20

2-Methoxy-13β-methyl-17β-pyranyloxy-17α-rhodanomethylgona-1,3,5(10),9(11)-tetraene.

The procedure described in Example 18 hereinbefore was repeated except that 1 gram of 3-methoxy-13β-methyl-17β-pyranyloxy-17α-rhodanomethylgona-1,3,5(10)-triene was substituted for the 3-methoxy-17β-methyl-17α-azidomethylgona-1,3,5(10)-trien-17β-ol in that example.

After conclusion of the electrolysis, the solution was evaporated to dryness and the residue was chromatographed as described in Example 14 using the same column that was described in Example 14, using fresh acid alumina granules and benzene as the eluent. The benzene eluate was concentrated and the residue was dissolved in and recrystallized from a mixture of dichloromethane and methanol. In this manner, 0.5 gram of 3-methoxy-13α-methyl-17β-pyranyloxy-17α-rhodanomethylogona-1,3,5-(10),9(11)-tetraene, having a melting point of 118-123° C and a specific optical rotation of +102.6° at a temperature of 25° C for the sodium D line, was obtained.

EXAMPLE 21

3-Methoxy-13β-methyl-17α-ethynylgona-1,3,5(10),9(11)-tetraene-17β-ol.

The procedure described in Example 18 hereinbefore was repeated except that 1 gram of 3-methoxy-13β-methyl-17α-ethynylgona-1,3,5(10)-trien-17β-ol was substituted for the 3-methoxy-13β-methyl-17α-azidomethylgona-1,3,5(10)-trien-17β-ol in that example.

In this manner, 0.6 gram of 3-methoxy-13β-methyl-17α-ethynylgona-1,3,5(10),9(11)-tetraen-17β-ol, having a melting point of 131°–132° C and a specific optical rotation of +71.7° at a temperature of 25° C for the sodium D line, was obtained.

EXAMPLE 22

3-Methoxy-13β-methyl-17α-cyanomethylgona-1,3,5(10),9(11)-tetraen-17β-ol.

A solution of 1 gram of 3-methoxy-13β-methyl-17α-cyanomethylgona-1,3,5(10)-trien-17β-ol and 0.6 gram of lithium perchlorate in 45 milliliters of N,N-dimethylformamide and 15 milliliters of methanol was electrolyzed with the same platinum electrodes that were described in Example 1 which were placed at the same distance from each other as in Example 1 with a current of 300 milliamperes for a period of 255 minutes.

The electrolyzed solution was then made slightly acid by the addition thereto of hydrochloric acid and allowed to stand at room temperature for a period between 20 and 30 minutes. Water was then added to the solution, whereupon 0.85 gram of 3-methoxy-13β-methyl-17α-cyanomethylgona-1,3,5(10),9(11)-tetraen-17β-ol having a melting point of 160-163° C precipitated and was separated therefrom. After recrystallization from a mixture of dichloromethane and n-hexane, the compound had a melting point of 164°–166° C and a specific optical rotation of +91.4° at a temperature of 25° C for the sodium D line.

EXAMPLE 23

3-Ethoxy-13β-methylgona-1,3,5(10),9(11)-tetraen-17-one.

A solution of 1 gram of 3-ethoxy-13α-methylgona-1,3,5(10)-trien-17-one, 1.1 milliliters of 2,6-dimethylpyridine, and 1.4 grams of tetraethylammonium perchlorate in 45 milliliters of N-N-dimethylformamide and 15 milliliters of methanol was electrolyzed with the same platinum electrodes that were described in Example 1 which were placed the same distance from each other as in Example 1 with a current of 600 milliamperes for a period of 25 minutes.

The electrolyzed solution was then made slightly acid by the addition thereto of hydrochloric acid and allowed to stand at room temperature for a period between 20 and 30 minutes. Water was then added to the solution, whereupon 0.9 gram of 3-ethoxy-13β-methylgona-1,3,5(10),9(11)-tetraen-17-one precipitated. After recrystallization from a mixture of dichloromethane and methanol, the compound had a melting point of 106°–107° C and a specific optical rotation of +252.7° at a temperature of 25° C for the sodium D line.

EXAMPLE 24

3-Methoxy-13β-methylgona-1,3,5(10),9(11)-tetraene-17β-spiro-1',2'-oxirane.

A solution of 1 gram of 3-methoxy-13β-methylgona-1,3,5(10)-triene-17β-spiro-1',2'-oxirane, 1.1 milliliter of 2,6 dimethylpyridine and 1.4 grams of tetraethylammonium perchlorate in 45 milliliters of N,N-dimethylformamide and 15 milliliters of methanol was electrolyzed between 2 electrodes spaced 1.5 centimeters apart, one a platinum anode having a surface of 21 square centimeters and the other a carbon cathode having a surface area of 8 square centimeters. The electrolysis was conducted with a current of 600 milliamperes for a period of 25 minutes.

All traces of methanol were distilled from the electrolyzed solution, which was then made slightly acid by the addition of hydrochloric acid and allowed to stand at room temperature for a period between 20 and 30 minutes, after which an aqueous sodium hydroxide solution was added thereto until the solution was alkaline. Upon addition of water to the solution, 0.7 gram of 3-methoxy-13β-methylgona-1,3,5(10),9(11)-tetraen-17β-spiro-1',2'-oxirane precipitated. When crystallized from a mixture of dichloromethane and methanol, 0.65 gram of the analytically pure compound having a melting point of 140°–143.5° C and a specific optical rotation of +123.3° at a temperature of 25° C for the sodium D line was obtained.

EXAMPLE 25

3-Acetoxy-13β-methylgona-1,3,5(10),9(11)-tetraen-17-one.

The procedure described in Example 1 was repeated except that 1 gram of 3-acetoxy-13β-methylgona-1,3,5(10)-trien-17-one was substituted for the 3-methoxy-13β-methyl-1,3,5(10)-trien-17-one in that example and the electrolysis was conducted with a current of 500 milliamperes from a period of 55 minutes.

Water was then added to the electrolyzed solution and it was then extracted with dichloromethane. The dichloromethane extract was dried over anhydrous sodium sulfate, saturated with hydrogen chloride gas and then allowed to stand for between 20 and 30 minutes at room temperature and then shaken three times with water. The dichloromethane phase was then separated from the aqueous phase, dried over anhydrous sodium sulfate, concentrated and the residue was chromatographed on silicate gel granules, using chloroform as eluent.

The first fraction contained 650 milligrams of 3-acetoxy-13β-methylgona-1,3,5(10),9 (11)-tetraen-17-one. This eluate was concentrated and the product was allowed to crystallize therefrom. After recrystallization from aqueous methanol, the analytically pure compound had a melting point of 123°–125° C and a specific optical rotation of +257.5° at a temperature of 25° C for the sodium D line.

EXAMPLE 26

3-Hydroxy-13β-methylgona-1,3,5(10),9(11)-tetraen-17-one.

The procedure described in Example 15 was repeated except that 1 gram of 3-methoxymethyleneoxy-13β-methylgona-1,3,5(10)-trien-17-one was substituted for the 3-methoxy-13β-methyl-17,17-(ethylenedioxy)gona 1,3,5(10)-triene in the example and the electrolysis was conducted for a period of 20 minutes with a current of 600 milliamperes.

The electrolyzed solution was then acidified with hydrochloric acid and the solution was heated under gentle reflux until the compound was completely hydrolyzed and all methoxymethyl ether was split from the compound. Water was then added to the solution and the precipitate was separated. In this manner, 0.75 gram of 3-hydroxy-13β-methylgona-1,3,5(10),9(11)-tetraen-17-one was obtained, which had a melting point of 250°–255° C after recrystallization from acetone.

EXAMPLE 27

3-Methoxy-13β-ethylgona-1,3,5(10),9(11)-tetraen-17-ol.

A solution of 950 milligrams of 3-methoxy-13β-ethylgona-1,3,5(10)-trien-17-ol, 1 milliliter of 2,6-dimethylpyridine and 980 milligrams of sodium perchlorate in 60 milliliters of methanol and 20 milliliters of dichloramethane was electrolyzed with the same platinum electrodes described in Example 1 spaced 1.5 centimeters apart from each other with a current of 500 milliampers for 26 minutes.

The electrolyzed solution was made slightly acid by addition of hydrochloric acid thereto and was allowed to stand at room temperature for a period between 20 and 39 minutes. The dichloromethane was then distilled off from the solution and water was added thereto to precipitate the product, which consisted of 700 milligrams of 3-methoxy-13β-ethylgona-1,3,5(10),9(11)-tetraen-17-ol, and which, upon recrystallization from aqueous ethanol, had a melting point of 61°–68° C and a specific optical rotation of +124° at a temperature of 25° C for the sodium D line.

EXAMPLE 28

3-Methoxy-13β-methylgona-1,3,5(10),9(11)-tetraene.

A solution of 570 milligrams of 3-methoxy-13β-methylgona-1,3,5(10)-triene, 0.5 milliliter of 2,6-dimethylpyridine, and 980 milligrams of sodium perchlorate in 60 milliliters of methanol and 20 milliliters of dichloromethane was electrolyzed with the same platinum electrodes described in Example 1 spaced 1.5 centimeters apart from each other with a current of 100 milliamperes for 67 minutes.

The electrolyzed solution was then made slightly acid by addition of hydrochloric acid thereto and was allowed to stand at room temperature for a period between 20 and 30 minutes. Water and dichloromethane were then added to the solution and the mixture was allowed to stratify and the dichloromethane layer was separated, dried over anhydrous sodium sulfate, and the solvents were distilled therefrom. The residue was then taken up in a mixture of acetone and methanol and the product was crystallized therefrom. In this manner, 350 milligrams of 3-methoxy-13β-methylgona-1,3,5(10),9(11)-tetraene, having a melting point of 83°-85.5° C and a specific optical rotation of +160.2° at a temperature of 25° for the sodium D line, was obtained.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A process for the production of a gona-1,3,5(10),9(11)-tetraene having the formula

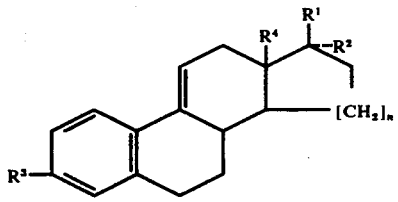

in which formula
n is 1 or 2,
$R^1$ is hydrogen, hydroxyl, alkoxy, alkanoyl or acetyl,
$R^2$ is hydrogen, alkoxy, acetoxy, alkenyl, alkinyl, or alkyl or is —CH$_2$X in which X is halogen, cyano or alkoxy,
or $R^1$ and $R^2$ together are oxo, methyleneoxy, or ethylenedioxy,
$R^3$ is hydroxyl, alkoxy of up to 4 carbon atoms, alkanoyl or alkoxymethyleneoxy, and
$R^4$ is methyl or ethyl,
which process comprises the steps of electrolyzing a gona-1,3,5(10)-triene having the formula

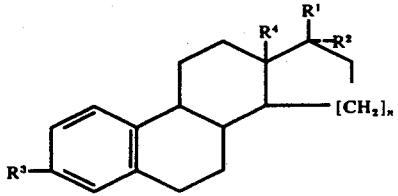

in which formula n, $R^1$, $R^2$, $R^3$, and $R^4$ have the same significance as hereinbefore, while dissolved or suspended in water or a primary or secondary alcohol or a mixture thereof, in the presence of an electroconductive salt which is non-reactive, under the conditions of the electrolysis with the gona-1,3,5(10)-triene, the cationic moieties of said electroconductive salts being ions of the alkali or alkaline-earth metals or cations of other metals and oxonium salts of elements of Groups V and VI of the Periodic Table, and the anionic moieties of the electroconductive salts being fluoborate, sulfate, perchlorate, arylsulfonate, alkylsulfonate, alkoxide, hexafluorophosphate, hydroxyl, nitrate, or carboxyl ions and the said electrolysis being conducted at a constant current or constant voltage until the conversion of the gona-1,3,5(10)-triene is complete so as to form a mixture of 9α and 9β- hydroxy or alkoxygona-1,3,5(10)-trienes having the respective formulae

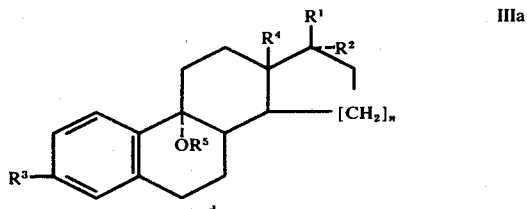

and

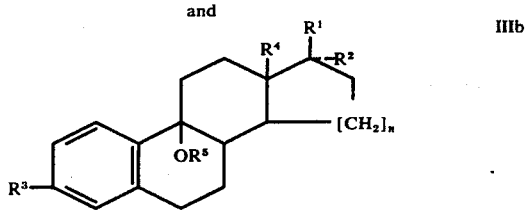

in which n, $R^1$, $R^2$, $R^3$, and $R^4$ have the same significance as hereinbefore, and $R^5$ depending on the solvent or suspension medium is hydrogen in case of water and is the corresponding alkyl group in case of an alcohol, and subsequently converting the said 9α or 9β-hydroxy or alkoxygona-1,3,5(10)-triene by means of an acid reagent to a gona-1,3,5(10),9(11)-tetraene.

2. A process as defined in claim 1 in which the 9α or 9β-hydroxy or alkoxygona-1,3,5(10)-triene is isolated from the electrolyzed solution before being converted to a gona-1,3,5(10),9(11)-tetraene.

3. A process as defined in claim 1 in which the electroconductive compound is a hydroxide or alkoxide of an alkali or alkaline-earth metal or a salt of an alkali or alkaline-earth metal and an acid of the group consisting of fluorboric, sulfuric, nitric, perchloric, hexafluorophoric, carboxylic, alkylsulfonic and arylsulfonic acids, or an oxonium salt of an element of group V or group VI of the Periodic Table.

4. A process as defined in claim 1 in which the solution that is electrolyzed contains a proton-acceptor of the group consisting of pyridine bases, salts of weak organic acids, or hydroxy or alkoxide ions.

5. A process as defined in claim 1 in which the solution that is electrolyzed contains a solubilizer of the group consisting of diethyl ether, tetrahydrofuran, dioxane, ethyl acetate, acetonitrile, N,N-dimethylformamide, dimethyl sulfoxide, acetone, methyl ethyl ketone, dichloromethane, chlorofrom, trichloroethylene, tertiary alchols, nitromethane and nitrobenzene.

6. A process as defined in claim 1 in which the solution is electrolyzed at a current density between 1 × 10$^{-4}$ and 0.1 ampere per square centimeter.

7. A process as defined in claim 1 in which the acid reagent that is used to convert the 9α or 9β-hydroxy or alkoxygona-1,3,5(10)-triene to a gona-1,3,5(10),9(11)-tetraene is an organic acid, a mineral acid, an acid alumina or a silica gel.

8. A process as defined in claim 1 in which the 9α- or 9β-hydroxy or alkoxygona-1,3,5(10)-triene is converted to the gona-1,3,5(10),9(11)-tetraene by directly reacting the solution or suspension of the said mixture of trienes after completion of the electrolyzing step to said acid reaction step without isolating said intermediate products defined in formulae IIIa and IIIb of claim 1.

9. A process as defined in claim 1 in which $R^5$ in the products is IIIa and IIIb hydrogen, methyl, ethyl, n-propyl or i-propyl.

* * * * *